United States Patent
Iversen et al.

(10) Patent No.: US 7,210,810 B1
(45) Date of Patent: May 1, 2007

(54) SURGICAL HEADLIGHT ASSEMBLY

(75) Inventors: Alfred A. Iversen, Wayzata, MN (US); Robert F. Spetzler, Paradise Valley, AZ (US); Andrew Iversen, Chanhassen, MN (US); Deron Singer, Shakopee, MN (US); Benjamin Osa, Edina, MN (US)

(73) Assignee: PMT Corporation, Chanhassen, MN (US)

( * ) Notice: Subject to any disclaimer, the term of this patent is extended or adjusted under 35 U.S.C. 154(b) by 0 days.

(21) Appl. No.: 11/221,094

(22) Filed: Sep. 6, 2005

Related U.S. Application Data

(60) Provisional application No. 60/607,174, filed on Sep. 3, 2004.

(51) Int. Cl.
*A61B 1/06* (2006.01)
*F21V 21/084* (2006.01)

(52) U.S. Cl. ...................................... 362/105; 362/804
(58) Field of Classification Search ................ 362/105, 362/804
See application file for complete search history.

(56) References Cited

U.S. PATENT DOCUMENTS

| | | | | |
|---|---|---|---|---|
| 4,593,683 A | * | 6/1986 | Blaha ......................... | 600/249 |
| 5,115,382 A | * | 5/1992 | Smith ......................... | 362/105 |
| 6,224,227 B1 | * | 5/2001 | Klootz ........................ | 362/105 |
| 6,457,838 B1 | * | 10/2002 | Dugmore et al. ........... | 362/106 |
| 6,896,389 B1 | * | 5/2005 | Paul ............................ | 362/105 |
| 6,955,444 B2 | * | 10/2005 | Gupta ........................ | 362/105 |
| 7,000,262 B2 | * | 2/2006 | Bielefeld ....................... | 2/418 |

OTHER PUBLICATIONS

VISILED, Halo Cordless Surgical Headlight, web pages, (c) 2005, VisiLED, Inc., U.S.
HEINE, 35 LED Head Light, web page, (c) 2005, Heine, Germany.
Welch Allyn, Superior White Light Precisely Where You Need It, product brochure, (c) 2003, Welch Allyn Medical Products, Skaneateles Falls, N.Y., U.S.

* cited by examiner

*Primary Examiner*—Alan Cariaso
*Assistant Examiner*—Leah S. Lovell
(74) *Attorney, Agent, or Firm*—Anthony G. Eggink; Katrina M. Eggink

(57) ABSTRACT

A surgical headlight assembly having a headset structure constructed of lightweight components. The headset structure has adjustable head strap members comprising a generally circular lateral band and a top band. A removable liner is attached to the inside surface of the adjustable headset structure. A lighting assembly which is adjustable with respect to the headset and which uses an adjustable LED is also provided connected to the lateral band. A battery pack is utilized to power the LED.

20 Claims, 4 Drawing Sheets

SURGICAL HEADLIGHT ASSEMBLY

This application claims the benefit of U.S. Provisional Patent Application Ser. No. 60/607,174, filed on Sep. 3, 2004.

BACKGROUND OF THE INVENTION

The present invention relates generally to a headlight assembly. Particularly, this invention relates to a surgical headlight assembly with an adjustable light assembly utilizing an LED.

Prior art surgical headlights have several disadvantages and limitations. For example, prior art assemblies typically utilize halogen or xenon bulbs which cause high ambient temperatures and require a cord to operate. The assemblies are also relatively heavy in weight, difficult to adjust and uncomfortable for the operator, such as a surgeon. Prior art headlight assemblies are also inefficient as to energy use and do not provide the true white light beneficial to distinguish color and to provide precise viewing, particularly as required for surgical use.

There is therefore a need in the surgical, medical and other arts for a lightweight portable and adjustable headlight assembly which overcomes the disadvantages and shortcomings of these prior art devices. The surgical headlight assembly of the present invention overcomes the problems and limitations of the prior art assemblies and provides an adjustable, energy efficient, light weight and effective headlight assembly for the surgical, medical, veterinary and related arts.

SUMMARY OF THE INVENTION

A surgical headlight assembly comprising a headset structure with lightweight components. The surgical headlight assembly comprises a unitary headset structure having a generally circular lateral headband or strap member and a top head strap or band member each having adjustment means and a light emitting diode (LED) lighting assembly with an easily switchable power source. The headband adjustment means may be ratchet gear adjustment structures, providing the wearer the ability to adjust and securely lock the headband size. To adjust the headband size, the user may depress and turn the ratchet knob. The headband may have removable interior linings constructed, for example, of Poron® foam or CoolMax® material with or without a silver woven liner or like lining materials. The headlight assembly further includes a vertical adjustment arm structure to provide easy adjustment of the lighting assembly with respect to the headset. The lighting assembly is attached to an attachment block means, mounted to the headset structure, or to a vertically pivotal joint or a multi-directional rotatable ball and socket joint.

The lighting assembly preferably has an adjustable housing having an LED. The lighting assembly further includes a filter and means to focus the light. A lens holder is provided on the lighting assembly which is movable to focus and change the light beam size. Various filters may be utilized, for example, to block UV light or to emit only black light, to thereby accommodate different uses.

The power source for the LED may be a battery pack with mounting means. Preferably, the battery source is a Lithium-Ion battery pack that is "hot swappable", i.e., it may be quickly replaced for continuous use. Further, the Lithium-Ion battery pack is also able to be quickly recharged, i.e., in 30 minutes. The battery or power source mounting means may permit the attachment of the battery pack to the waist or to the headband, for example, with the use of a battery clip and a battery nest. The battery nest may utilize a spring loaded ball plunger to help secure the battery pack onto the headband or headgear. Further, loupes, or other magnification lenses worn by a user during surgery, may be attached to the headlight assembly of the invention.

The surgical headlight of the present invention is constructed and arranged for surgical use and for other uses in the medical and veterinary arts, for example, including examination and laboratory use relating to dermatology, gynecology and the like as well as in other arts. Utilizing an LED, i.e., 3 watts, the headlight radiates white brightness and true lighting (i.e., LED providing a color range of approximately 4,800 to 6,000K) to show clarity and colors beneficial in surgical applications. The use of an LED light accommodates the surgeon by providing excellent lighting using lightweight materials, emitting low heat and operating without a cord.

It is a benefit of the present invention to provide an ergonomically constructed headband for adjustable positioning on the user's head to provide a secure and comfortable fit. It is another benefit of the present invention to provide a lighting means which is economical and has a long life and a low operating cost. It is another benefit of the present invention to provide the use of multiple LEDs for a higher intensity and the ability to use a filter, optical lenses or mechanical means to combine the light beams to form one uniform beam and to optimize the light beam size and light intensity. It is yet another benefit to dissipate heat from the device by incorporating cooling vents, a cooling fan, a heatsink and/or a thermal collecting insert into the headlight structure.

These and other benefits of this invention will become clear from the following description by reference to the drawings.

DESCRIPTION OF THE PREFERRED EMBODIMENTS

The surgical headlight assembly of the present invention comprises an LED lighting assembly with a power assembly, ergonomic headgear, and adjustment mechanisms for adjusting the headgear and the housing holding the LED. The LED lighting assembly may be adjustable with respect to the headgear and contains a lens for focusing or concentrating the emitted light. The adjustment knobs of the headgear allow for custom fitting on the user, i.e., on the head of a surgeon. The LED may be a 3 watt LED, for example. The LED unit preferably has cooling vents, a fan assembly or a thermal collecting insert to dissipate heat from the LED unit.

Figure 1:
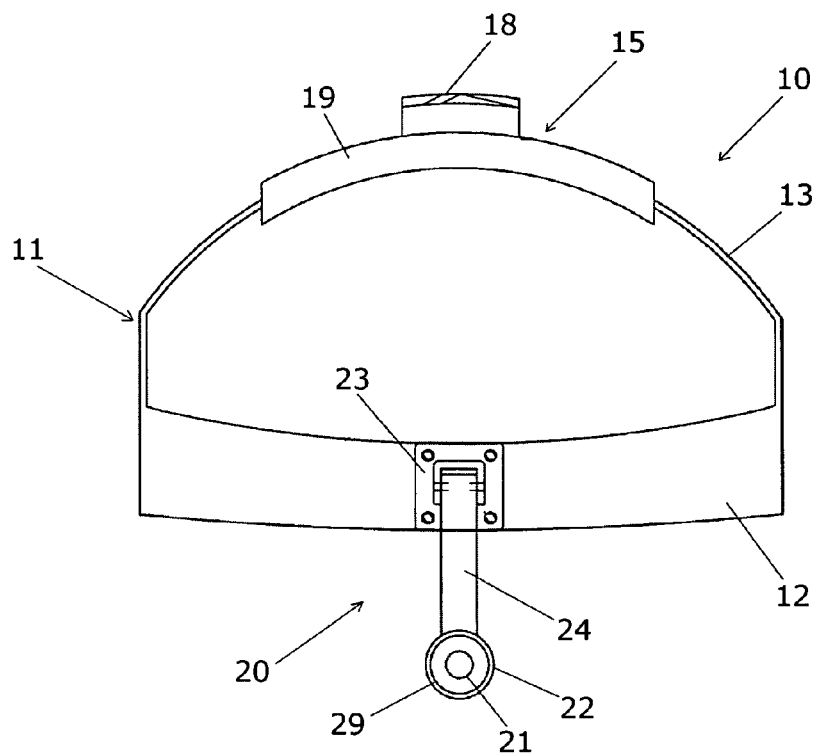
FIG. 1 is a front plan view showing the surgical headlight assembly of the invention.
Figure 2:
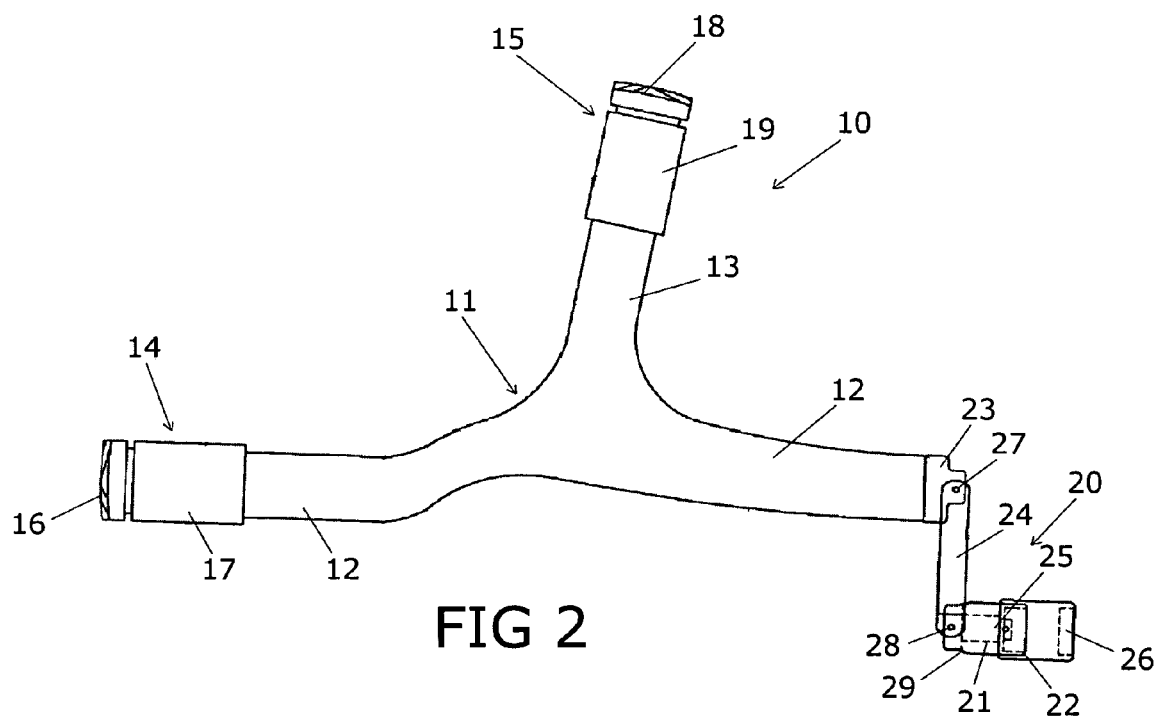
FIG. 2 is a side plan view of the surgical headlight assembly of FIG. 1.
Figure 3:
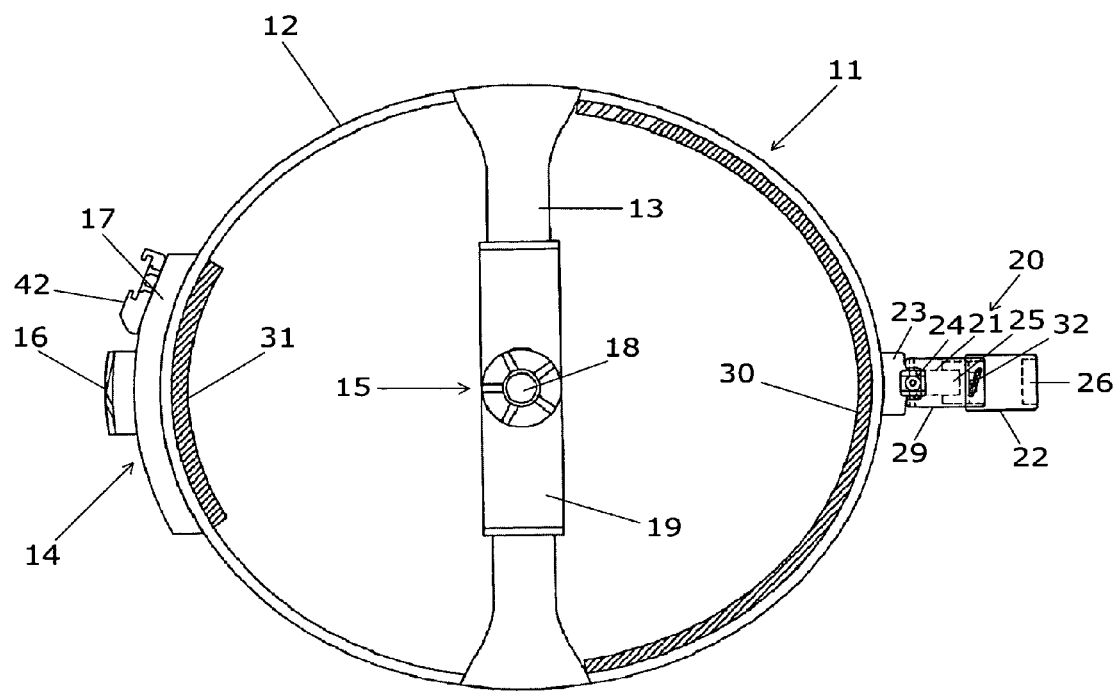
FIG. 3 is a top plan view of the surgical headlight assembly of FIG. 1.

Referring to FIGS. 1–3, the surgical headlight assembly 10 comprises a headset structure 11 having a flexible, generally circular, lateral band or strap 12 and a top head strap 13. Lateral strap 12 is shown having adjustment structure 14 and top head strap 13 is shown having adjustment structure 15. Battery nest 42 is shown attached to adjustment structure 14 for receiving power assembly 34, shown and discussed below with respect to FIGS. 7–11. Lighting assembly 20 is shown attached to the front of lateral strap 12 using attachment structure or block 23. Although attachment block 23 is shown as a vertically pivoting member, other attachment means, for example, a ball-and-socket multi-directionally rotatable attachment structure and like structures are within the purview of this invention. Adjustment structure or arm 24 is shown connecting the attachment block 23 and the lighting assembly 20 so that the position and angle of the lighting assembly may be adjusted with respect to the attachment block 23 fixed to the lateral strap 12 of headset structure 11. Pivot points 27 and 28 are shown to provide such vertical, outward and rotational movement of the lighting assembly with respect to headset structure 11.

Lighting assembly 20 comprises a tubular lighting housing or covering 21 and an adjustable, tubular filter or lens housing structure in which it is positioned. The lighting housing 21 houses or covers a light source 25, preferably an LED. The lens housing is generally tubular in structure and is comprised of inner housing 29 and outer housing 22 which is rotatable with respect to inner housing 29. Outer housing 22 is constructed and arranged to house a lens or filter structure 26 positioned at its outer or distal end. In use, outer housing 22 is rotated with respect to inner housing 29 using thread structure 32, shown in FIG. 3, thereby moving the lens closer to or further from the light source 25, to thereby focus and/or intensify the light beam. The thread structure 32 is shown to be a curved thread segment between inner housing 29 and outer housing 22 whereby the turning of outer housing 22 results in the rotational and linear movement of lens or filter 26 with respect to inner housing 29. The generally tubular inner housing 29 annularly surrounds tubular lighting housing 21 and is attached at the bottom of adjustment structure 24 at pivot point 28. Further, loupes, or other magnification lenses worn by a user during surgery, may be attached to the headlight assembly of the invention on, near or adjacent the inner housing 29.

Figure 4:
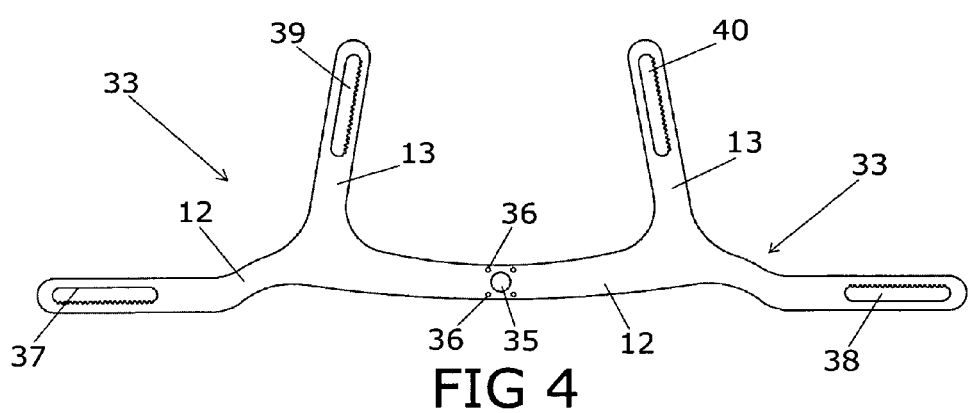
FIG. 4 is a plan view of the headset band structure of the surgical headlight assembly of the invention.
Figure 5:
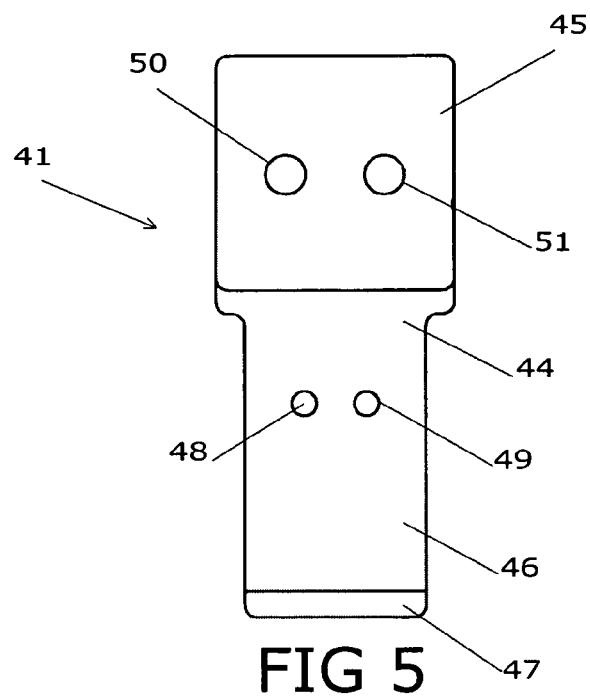
FIG. 5 is a front plan view of the battery clip of the invention.
Figure 6:
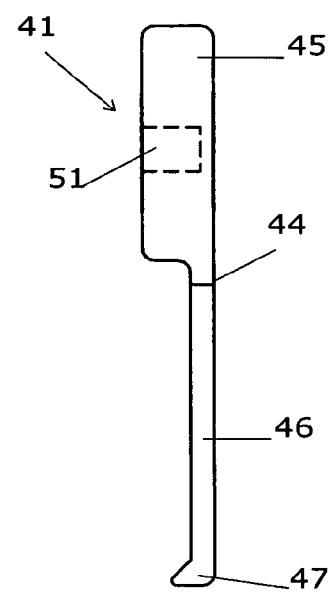
FIG. 6 is a side plan view of the battery clip of FIG. 5.

Lateral band or strap 12 is shown having adjustment structures 14 and top strap 13 is shown having adjustment structure 15, providing the wearer the ability to lock and to adjust the headband size. The adjustment structures 14 and 15 are preferably ratchet gear adjustment structures. The adjustment structures 14 and 15 comprise buckles 17 and 19 and knobs 16 and 18. FIG. 4 shows flexible, unitary headset body member 33, having upwardly extending members which comprise top strap 13 and which contain apertures 39 and 40 and left and right extending members which comprise lateral headband 12 and which contain apertures 37 and 38. As shown, apertures 37–38 and 39–40 have ratchet protrusions along one side so that when positioned adjacent each other to form bands 12 and 13, respectively, ratchet protrusions are located along the top and bottom of the opening formed. Buckle members 17 and 19 may then be placed cooperating with the formed apertures of the band members to hold the band together. In order to adjust the lateral headband or top band size, the user depresses and turns knob 16 or 18 which moves along the ratchet protrusions of apertures 37–40 contained within the buckle members 17 and 19, respectively. Further shown in FIG. 4, is opening 35 through which wire may run to provide power to the light source and apertures 36 for use with fasteners to secure the attachment structure or block 23 to the headset structure 11.

As shown in FIG. 3, lateral headband 12 has interior liner 30 positioned for the forehead of the wearer and interior liner 31 positioned for the back of the wearer's head. Liners 30 and 31 are removable and replaceable and are preferably constructed of a soft, compressible and conforming material, i.e., Poron® (polyurethane) foam, CoolMax® liner, CoolMax® liner woven with silver and like liner materials. The liner may further be textured for breathability and ease in conforming to a user's head. A liner may also be positioned along the underside of top band 13 or at any location along the inside of the headset structure 11 for the wearer's comfort. The removable liners may be attached using a hook and loop fastener system, adhesive or the like. The unitary headset structure is preferably constructed of a flexible material, for example, a flexible polymeric material, i.e. polyethylene, polypropylene and like materials.

Figure 8:
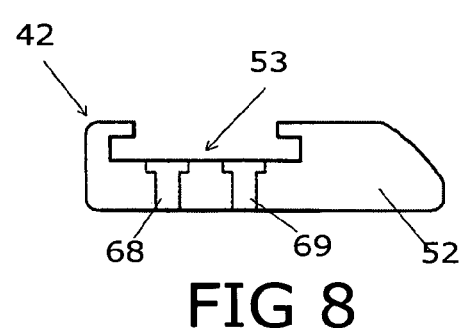
FIG. 8 is a side plan view of the battery clip of FIG. 7.
Figure 9:
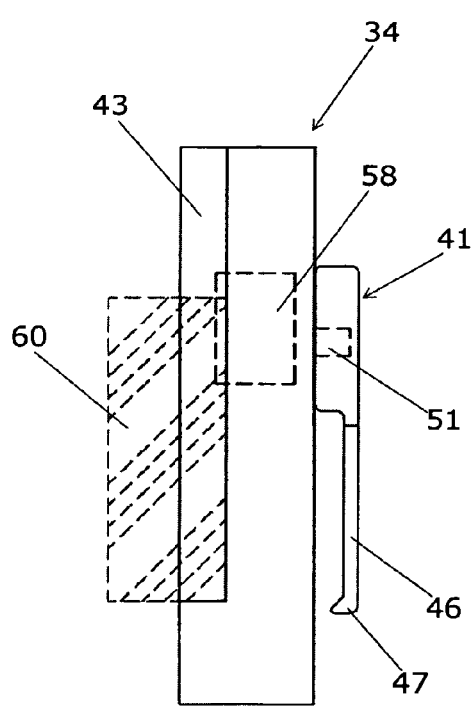
FIG. 9 is a side plan view of the power assembly of the invention showing the battery dock, battery and battery clip.
Figure 10:
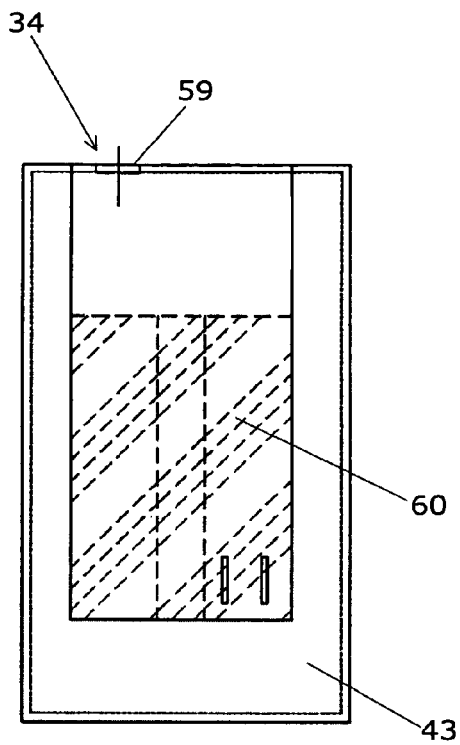
FIG. 10 is a front plan view of the power assembly of FIG. 9.
Figure 11:
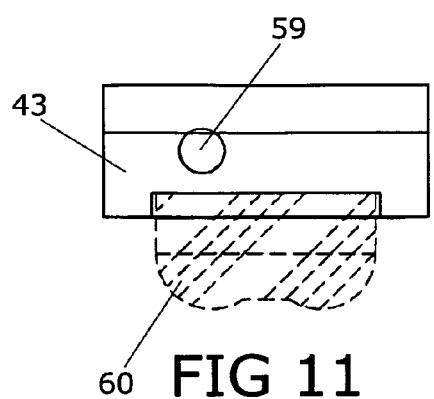
FIG. 11 is a top plan view of the battery dock and battery of FIG. 9.

FIGS. 5–6 and FIGS. 9–11 show the power assembly 34 and waist attachment or battery clip 41. Battery clip 41 is shown having body 44 with upper portion 45 and lower portion 46 having thickened end or lip 47. Lower portion 46 is constructed and arranged to slide into aperture 53 of battery nest 42, shown in FIGS. 1 and 7–8, to position power assembly 34 on headset 11. Apertures 50 and 51 are shown positioned within upper portion 45 and apertures 48 and 49 are shown extending through lower portion 46. FIG. 9 shows power assembly 34 comprising battery clip 41 attached to battery dock 43, using apertures 50 and 51. Battery dock 43 is shown having on/off switch 58 and may be secured to a users clothing using the clip formed between the back of battery dock 43 and the lower portion 46 of battery clip 41. Referring to FIGS. 10–11, battery pack 60 is shown in communication with battery dock 43. Power plug adapter 59 is shown disposed along the top of battery dock 43.

Figure 7:
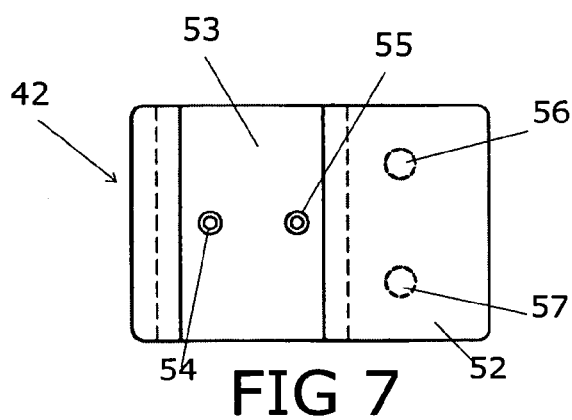
FIG. 7 is a front plan view of the battery nest of the invention.

To provide headset attachment means for power assembly 34, FIGS. 7–8 show battery nest 42 which is constructed and arranged to attach to headset 11, preferably on the outside of buckle 17 of attachment structure 14 (as shown in FIG. 1), using fasteners (not shown) through apertures 56 and 57. Battery nest 42 is shown having body 52 having indented portion 53 which is constructed and arranged having spring loaded ball plungers 54 and 55, contained by apertures 68 and 69, to cooperate with apertures 48 and 49, shown in FIG. 5, to thereby receive and secure the lower end 46 of battery clip 41 within indented or channel portion 53.

Figure 12:
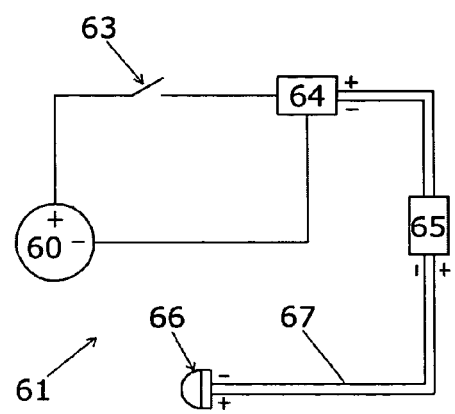
FIG. 12 is a schematic diagram of the circuitry of the invention.

As shown in circuitry diagram 61 of FIG. 12, power is supplied to the LED light source 66 by battery pack 60 when the power switch 63 is activated, completing the circuit with the circuit regulator 64. The regulator 64 provides a constant current, i.e. approximately 1 amp, to thereby control the input voltage, i.e. approximately 3.9 volts, to the LED. Conductive wire 67 runs from the power plug adapter 65 to the LED 66. In the headlight assembly of the invention, conductive wire preferably runs from the LED, through opening 35, and out of sight behind liner 30 along the headset structure 11, through an opening (not shown) in the side of headset 11 for connection to the power plug adapter 59 of battery dock 43 located on battery nest 42 on the back of headset 11. Alternatively, if a user desires to wear the power assembly on clothing, i.e., a belt, a longer wire is provided for attachment between wire 67 and the power plug adapter of the battery dock.

The surgical headlight assembly of the invention may be provided to a user in a kit. The surgical headlight assembly kit would include the flexible, adjustable head set structure having the lighting assembly and battery nest attached thereto, two battery packs, one battery pack charger, a battery dock with clip attached thereto and two conductive wires of varying lengths. It is within the purview of the present invention to utilize other and newly improved LED's, batteries or other power outputs, power chargers and power assemblies as components in the surgical headlight assembly.

The surgical headlight is manufactured by assembling various cooperating lightweight components. These components include the lightweight, flexible polymeric straps, i.e., polyethylene, to form the headgear, adjusting components for the headgear, the LED bulb unit and a battery compartment. Although lightweight thermoplastic materials are preferred, other lightweight materials may be utilized according to the teachings of the present invention. Alternatively, for example, soft headbands, whether of a polymeric, woven, elastic or other material, may be utilized within the purview of the present invention and which may alleviate the need for adjustment structures and liners or utilize other adjustment means, i.e., hook and loop fasteners. In the latter configuration, the lighting assembly may be mounted to a rigid member attached to the front of the headband, for example.

The headlight assembly or headgear may be produced via heat stamping, die cutting, laser cutting, plastic injection molding and like processes. The LED casing, adjustment components, and focusing lenses are preferably injection molded. The circuitry in the LED lamp may be soldered and tested for functionality. After the LED lamp unit is assembled, it is then attached to the front of the headgear. The conducting wires are preferably guided invisibly along the side of the headgear into the battery pack. A hot-swappable Lithium-Ion battery pack is preferably used to power the LED light.

To use the surgical headlight assembly of the invention all the components of the headlight should be properly assembled and in good condition. The on/off switch should be tested to ensure that the LED is working and the light emitted is sufficient. A replacable, disposable absorbent material, i.e., Poron® foam, CoolMax® material, silver woven CoolMax® material (manufactured by DuPont) or other liner materials, may be placed on the inside of the headset structure of the headlight assembly. The headlight assembly may be placed on the head of the operator and adjusted to fit using the adjustment knobs or similar adjustment means. As shown, the headset assembly preferably has dual adjustment means. The fit of the head strap is preferably snug without any looseness or slippage. The LED may be turned on, its position adjusted and the light focused to the operator's preference.

The wire connection between the battery pack and the headset may be provided in specified lengths, retractable or of the "recoil wire" type to thereby minimize the length of exposed wire on or to the headset. The battery pack is preferably a compact structure, so that it may be adapted for attachment to either the waist, for example, or to the headgear structure. Further, the battery pack is preferably quickly recharged in approximately 30 minutes.

As many changes are possible to the surgical headlight assembly of this invention, utilizing the teachings thereof, the description above and the accompanying drawings should be interpreted in the illustrative and not the limited sense.

That which is claimed is:

1. A surgical headlight assembly comprising:
    a) an adjustable and flexible headset structure, said headset structure having a headband member and a top strap member, said headband and top strap members each having a length adjustment means comprising a ratchet gear adjustment means;
    b) a light emitting housing structure having connection means to said headband member; said light emitting housing structure having an LED and a lens member, wherein said lens member is horizontally adjustable with respect to said LED and wherein said light emitting structure is adjustable with respect to said headset structure, wherein said connection means of said light emitting structure includes a pivotable arm structure and an attachment block, wherein said attachment block is mounted to said headset structure and wherein said pivotable arm structure has two pivotal ends, wherein one end is in pivotal and rotational communication with said attachment block and wherein said light emitting structure is pivotally disposed at the other end of said pivotable arm structure which thereby provides vertical and rotational adjustment means for said light emitting structure with respect to said headset structure; and
    c) a power source for said LED.

2. The surgical headlight assembly of claim 1, wherein said light emitting structure is comprised of an inner housing for containing said LED and an outer housing for containing said lens member, wherein said outer housing is threadedly connected to and rotatable with respect to said inner housing, thereby permitting the controlled linear movement of said lens structure with respect to said LED.

3. The surgical headlight assembly of claim 1, wherein said power source is a rechargeable, hot-swappable Lithium-Ion battery pack.

4. The surgical headlight assembly of claim 1, wherein said attachment block and said end of said pivotable arm structure form a ball and socket configuration.

5. The surgical headlight assembly of claim 1, wherein said headset structure is constructed of a unitary polymeric structure having two top straps and two lateral straps, each of said top straps and said lateral straps having an elongated aperture with inwardly disposed ratchet protrusions, said headset structure forming said head band member and said top strap member of said headset structure.

6. A surgical headlight assembly comprising:
    a) a flexible headset structure having a generally circular lateral band and a top band connected thereto said lateral band and said top band having inner and outer surfaces, said generally circular lateral band having an attachment block structure connected to said outer surface of said lateral band, said attachment block structure further having a socket disposed therein;
    b) adjustment means comprising a ratchet gear adjustment structure and an operating knob operative to adjust the size of said lateral band and adjustment means comprising a ratchet gear adjustment structure and an operating knob operative to adjust said top band;

c) a removable liner attached to the inside surface of said circular lateral band and to said inside surface of said top band;
d) an adjustable arm structure having a first end and a second end, wherein a ball member is located at said first end and is constructed and arranged for rotational movement within said socket of said attachment block structure,
e) an adjustable lighting assembly connected to and extending from said lateral band, said lighting assembly further comprising an adjustable housing structure located at one end of said pivoting arm assembly and having an LED mounted therein, wherein said adjustable housing structure comprises an inner housing for containing said LED and an outer housing for containing a lens, wherein said outer housing is threadedly connected to and rotatable with respect to said inner housing, thereby allowing the controlled linear movement of said lens with respect to said LED;
f) power means in communication with said LED, said power means having an attachment structure; and
g) a nest structure secured to said generally circular lateral band, said nest structure being constructed and arranged having a receiving slot member to receive said attachment structure of said power means.

7. The surgical headlight assembly of claim 6, wherein said housing structure further has a filter located at the distal end of said outer housing.

8. The surgical headlight assembly of claim 6, wherein said attachment structure is a clip member and wherein said nest structure further having spring loaded ball plungers in said receiving slot to secure said clip member and wherein said power means is attachable to a user or to said nest structure of said headset structure.

9. The surgical headlight assembly of claim 6, wherein said power means includes rechargeable batteries and wherein said lighting assembly comprises at least one LED providing a color range of approximately 4800 to 6000K.

10. The surgical headlight assembly of claim 6, wherein said housing has cooling means selected from the group of cooling means consisting of cooling vents, a cooling fan and a heat sink.

11. The surgical headlight assembly of claim 6, wherein said power means includes a circuit regulator and an on/off switch.

12. The surgical headlight assembly of claim 6, wherein said removable liner comprises polyurethane or a CoolMax liner.

13. The surgical headlight assembly of claim 6, wherein said headset structure is constructed of a unitary polymeric structure having two top strap members and two lateral members, each said top strap member and said lateral member having an elongated aperture with inwardly disposed ratchet protrusions, said unitary polymeric structure forming said lateral band and said top band of said headset structure.

14. A surgical headlight assembly comprising:
a) a headset structure, said headset structure having a headband member and a top strap member, said headband and top strap members each having an adjustment means;
b) a light emitting structure having connection means to said headband member; wherein said connection means includes a pivotable arm structure and an attachment block, wherein said attachment block includes a socket portion and is connected to said headset structure and wherein said pivotable arm structure has two pivotal ends, wherein one end is a ball portion and is in rotational communication with said socket portion of said attachment block and wherein said light emitting structure is pivotally disposed at the other end of said pivotable arm structure which thereby provides vertical and rotational adjustment means for said light emitting structure with respect to said headset structure, said light emitting structure further having an inner housing to house a light source and an outer housing to house a lens member, wherein said outer housing is threadedly connected to and rotatable with respect to said inner housing; and
c) a power source for said light source.

15. The surgical headlight assembly of claim 14, wherein said adjustment means of said headband and top strap members is a ratchet gear adjustment means.

16. The surgical headlight assembly of claim 14, wherein said headband has an inside and an outside and wherein said inside includes at least one portion of replaceable liner, wherein said liner is selected from the group of liners consisting of a Poron® liner, a CoolMax® liner and a CoolMax® woven with silver liner.

17. The surgical headlight assembly of claim 14, wherein said light source is at least one LED.

18. The surgical headlight assembly of claim 14, wherein said light emitting structure includes cooling means.

19. The surgical headlight assembly of claim 18, wherein said cooling means is selected from the group consisting of a heatsink, a cooling fan, a thermal cooling insert, at least one air vent, and combinations thereof.

20. The surgical headlight assembly of claim 14, wherein said power source is a rechargeable, hot-swappable Lithium-Ion battery pack.

* * * * *

UNITED STATES PATENT AND TRADEMARK OFFICE
CERTIFICATE OF CORRECTION

PATENT NO.         : 7,210,810 B1                                  Page 1 of 1
APPLICATION NO.    : 11/221094
DATED              : May 1, 2007
INVENTOR(S)        : Alfred A. Iversen et al.

It is certified that error appears in the above-identified patent and that said Letters Patent is hereby corrected as shown below:

Please delete the following from Claim 8 (Column 7, Lines 32-34):

--and wherein said power means is attachable to a user or to said nest structure of said headset structure--

Signed and Sealed this

Twenty-sixth Day of June, 2007

JON W. DUDAS
*Director of the United States Patent and Trademark Office*